US012370290B2

(12) United States Patent
Chow et al.

(10) Patent No.: US 12,370,290 B2
(45) Date of Patent: *Jul. 29, 2025

(54) 3D-PRINTED SCAFFOLDS OF PEPTIDE CONJUGATE POLYMER

(71) Applicant: Lehigh University, Bethlehem, PA (US)

(72) Inventors: Lesley W. Chow, Bethlehem, PA (US); Hannah L. Dailey, Neshanic Station, NJ (US); Hafiz Busari, Greenville, SC (US); Peter Schwarzenberg, Fountain Hill, PA (US); Katherine Hudson, Hopkinton, MA (US)

(73) Assignee: Lehigh University, Bethlehem, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/537,336

(22) Filed: Dec. 12, 2023

(65) Prior Publication Data
US 2024/0115771 A1   Apr. 11, 2024

Related U.S. Application Data

(63) Continuation of application No. 16/632,992, filed as application No. PCT/US2018/043262 on Jul. 23, 2018, now Pat. No. 11,839,699.
(Continued)

(51) Int. Cl.
*A61L 27/54* (2006.01)
*A61L 27/18* (2006.01)
(Continued)

(52) U.S. Cl.
CPC .............. *A61L 27/54* (2013.01); *A61L 27/18* (2013.01); *A61L 27/58* (2013.01); *B29C 64/106* (2017.08); *B33Y 10/00* (2014.12); *B33Y 70/00* (2014.12); *B33Y 80/00* (2014.12); *A61L 2430/02* (2013.01); *A61L 2430/06* (2013.01); *A61L 2430/10* (2013.01); *A61L 2430/24* (2013.01); *B29K 2067/00* (2013.01); *B29K 2089/00* (2013.01); *B29L 2031/7532* (2013.01)

(58) Field of Classification Search
None
See application file for complete search history.

(56) References Cited

U.S. PATENT DOCUMENTS

| | | | |
|---|---|---|---|
| 7,968,026 B1 | 6/2011 | Teoh et al. | |
| 8,071,007 B1 | 12/2011 | Teoh et al. | |
| 11,839,699 B2 * | 12/2023 | Chow | B33Y 10/00 |

FOREIGN PATENT DOCUMENTS

WO   WO 2016/176444 A1   11/2016

OTHER PUBLICATIONS

Lesley W. Chow et al.: "Peptide-Directed Spatial Organization of Biomolecules in Dynamic Gradient Scaffolds", Adv. Healthcare Mater. 2014, 3, 1381-1386 (Year: 2014).*
(Continued)

*Primary Examiner* — Mohammad M Ameen
(74) *Attorney, Agent, or Firm* — The Belles Group, P.C.

(57) ABSTRACT

Described herein is a 3D-printed scaffold comprising a peptide-polymer conjugate, the peptide-polymer conjugate having the structure: X—Y—Z—Y—X, wherein X is a biologically active peptide, Y is a linker moiety, and Z is a biocompatible and biodegradable polymer.

19 Claims, 8 Drawing Sheets

Related U.S. Application Data

(60) Provisional application No. 62/535,955, filed on Jul. 23, 2017.

(51) Int. Cl.

| | |
|---|---|
| *A61L 27/58* | (2006.01) |
| *B29C 64/106* | (2017.01) |
| *B33Y 10/00* | (2015.01) |
| *B33Y 70/00* | (2020.01) |
| *B33Y 80/00* | (2015.01) |
| *B29K 67/00* | (2006.01) |
| *B29L 31/00* | (2006.01) |

(56) References Cited

OTHER PUBLICATIONS

Joao F M Ribeiro et al.: "Structural monitoring and modeling of the mechanical deformation of three-dimensional printed poly(-caprolactone) scaffolds", Biofabrication 9 (2017) 025015 (Year: 2017).*

International Search Report and Written Opinion issued for PCT/US2018/043262, mail date Oct. 15, 2018, pp. 1-14.

Chow et al. "Peptide-directed spatial organization of biomolecules in dynamic gradient scaffolds," Advanced Healthcare Materials, Feb. 24, 2014 (Feb. 24, 2014), vol. 3, pp. 1381-1386.

Ribeiro et al. "Structural monitoring and modeling of the mechanical deformation of three-dimensional printed poly(E-caprolactone) scaffolds," Biofabrication, May 11, 2017 (May 11, 2017), vol. 9, pp. 1-13.

He et al. "An Investigation of the Behavior of Solvent based Polycaprolactone ink for Material Jetting," Sci Rep, Feb. 12, 2016 (Feb. 12, 2016), vol. 6, pp. 1-10.

Chow, L.W. "Chapter 3: Electrospinning Functionalized Polymers for Use as Tissue Engineering Scaffolds," Biomaterials for Tissue Engineering: Methods and Protocols, Methods in Molecular Biology, Apr. 21, 2018 (Apr. 21, 2018), K. Chawla (ed.), vol. 1758, pp. 27-39.

Hansske Felix et al : "Via precise interface engineering towards bioinspired composites with improved 3D printing processability and mechanical properties" Journal of Materials Chemistry. B, vol. 5, No. 25, May 30, 2017 (May 30, 2017), pp. 5037-5047.

Chow et al. "Peptide-directed spatial organization of biomolecules in dynamic gradient scaffolds," Advanced Healthcare Materials, vol. 3, No. 9, Sep. 1, 2014 (Sep. 1, 2014), pp. 1381-1386.

Joao F M Ribeiro et al : "Structural monitoring and modeling of the mechanical deformation of three-dimensional printed poly ([epsilon] -caprolactone) scaffolds", Biofabri Cation, vol. 9, No. 2, May 11, 2017 (May 11, 2017), pp. 1-13.

A. Gloria et al. : "Three-dimensional Poly(e-caprolactone)bioactive scaffold with controlled structural and surface properties", Biomacromolecules 13. 11 (2012): 3510-3521 (Year: 2012).

Harrison et al. "Modular and Versatile Spatial Functionalization of Tissue Engineering Scaffolds through Fiber-Initiated Controlled Radical Polymerization," Adv Fune! Mater, Aug. 17, 2015 (Aug. 17, 2015), vol. 25. pp. 5748-5757.

Trachtenberg et al. "Open-source three-dimensional printing of biodegradable polymer scaffolds for tissue engineering, " J Biomed Mater Res A, Dec. 1, 2014 (Dec. 1, 2014), vol. 102, pp. 4326-4335.

* cited by examiner

3D-PRINTED SCAFFOLDS OF PEPTIDE CONJUGATE POLYMER

CROSS-REFERENCE TO RELATED APPLICATIONS

This application is a continuation of U.S. application Ser. No. 16/632,992, filed Jan. 22, 2020, which is a national stage entry under 35 U.S.C. § 371 of International Patent Application No. PCT/US2018/43262, filed Jul. 23, 2018, which in turn claims the benefit of priority from U.S. Provisional Patent Application No. 62/535,955, filed Jul. 23, 2017, the contents of which are hereby incorporated herein by reference in their entireties.

BACKGROUND

Osteoarthritis is a degenerative condition that impacts over 70% of adults over the age of 65. This disease is characterized by a painful breakdown of the articular cartilage that covers the bone ends and lubricates the motion of the joints. Currently, treatment for end-stage osteoarthritis is arthroplasty, or total joint replacement. More than 50% of total joint replacement patients are under age 65, presenting a significant challenge to the health system because these patients are expected to outlive their implants and may require one or more revision procedures over their lifetime. The cost of this care presents a staggering economic burden. The financial burden of joint replacement and the individual patient hardship during the painful rehabilitation period provide significant motivation to repair and regenerate cartilage tissue. Thus, there exists a need for a new approach at treating osteoarthritis as well as other orthopedic related ailments.

SUMMARY

According to some embodiments, the present invention is directed to a 3D-printed scaffold comprising a peptide-polymer conjugate, the peptide-polymer conjugate having the structure: X—Y—Z—Y—X; wherein X is a biologically active peptide, Y is a linker moiety, and Z is a biocompatible and biodegradable polymer.

In other embodiments, the present invention is directed to an implantable scaffold comprising: a first layer formed of a plurality of first fibers oriented in a first direction; and a second layer formed of a plurality of second fibers oriented in a second direction; wherein the first direction and the second direction are different and the pluralities of first and second fibers comprise peptide-polymer conjugate.

Other embodiments of the present invention include a method of forming an implantable scaffold comprising: a) 3D-printing a plurality of first fibers in a first direction to form a first layer; b) 3D-printing a plurality of second fibers in a second direction atop the first layer to form a second layer, wherein the first and second directions are different; wherein the first and second fibers comprise peptide-polymer conjugate.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

Figure 1:
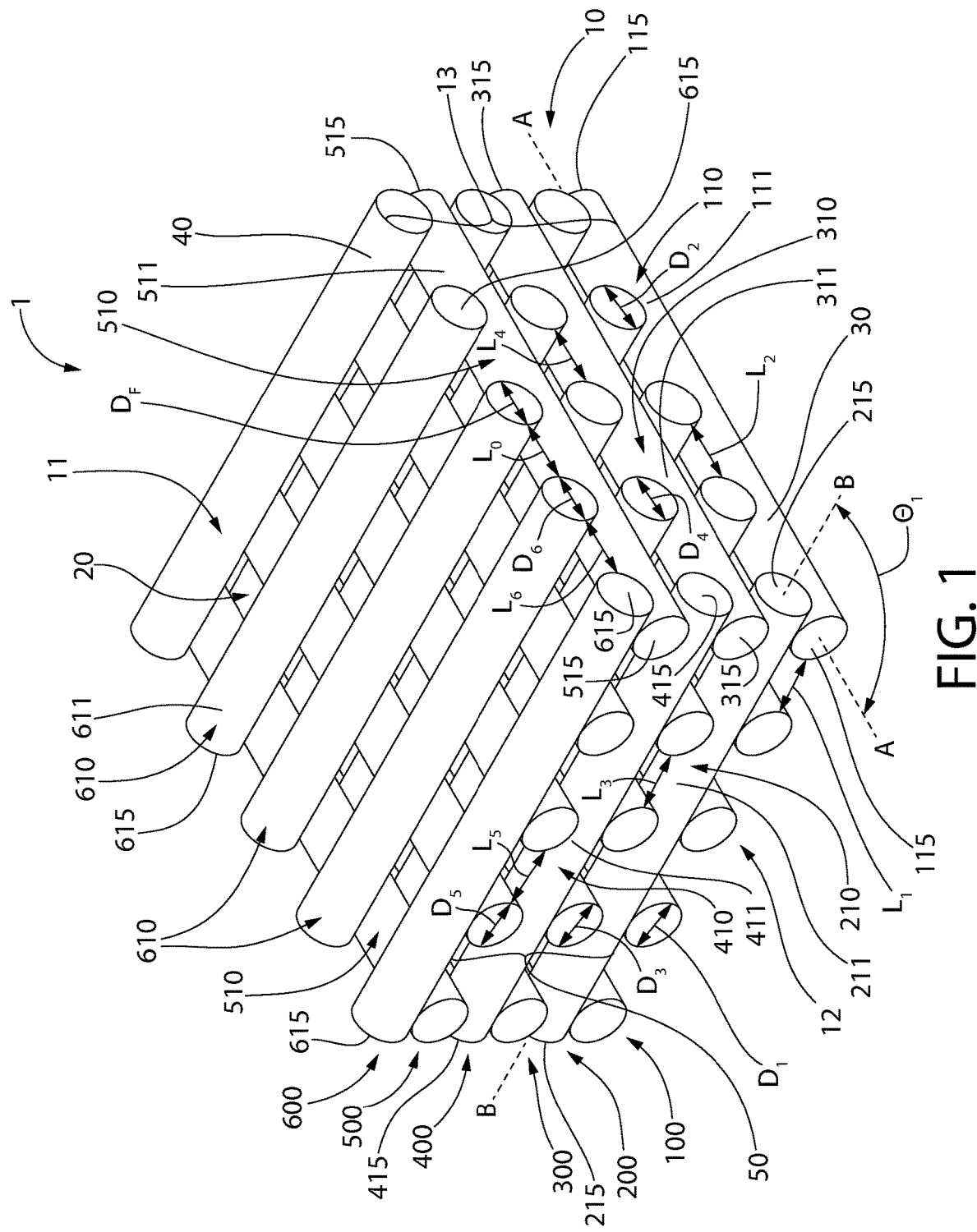
FIG. 1 is a perspective close-up view of a scaffold according to one embodiment of the present invention.

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top," and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such.

Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Unless otherwise specified, all percentages and amounts expressed herein and elsewhere in the specification should be understood to refer to percentages by weight. The amounts given are based on the active weight of the material. According to the present application, the term "about" means+/−5% of the reference value. According to the present application, the term "substantially free" less than about 0.1 wt. % based on the total of the referenced value.

The present invention is directed to peptide-polymer conjugates, methods of their production, as well as musculoskeletal tissue engineering that comprise the peptide polymer conjugates. In some embodiments, the peptide-polymer conjugates of the present invention are used in the design and manufacture of cell-free scaffolds for regeneration of musculoskeletal tissues and interfaces. The scaffolds of the present invention may suitable for, but are not limited to, implantation in cartilage, bone, tendon, ligament, fibrous joints, or connective tissue, and boundary zones between. Tissues. In a non-limiting example, the scaffold may be implantable into a bound zone between tissue that includes the osteochondral zone, which refers to the transition region from cartilage to underlying bone. Other cell-free scaffold-based tissue engineering applications may extend beyond the musculoskeletal system The peptide-polymer conjugates and 3D-printed scaffolds formed thereof may also be suitable for cell-based therapies, such as mesenchymal stem cells that are harvested and cultured within the scaffold, followed by autologous re-implantation—as discussed further herein.

Referring now to FIG. 1, the present invention is directed to a scaffold 1 comprising a multi-layered structure 10. The scaffold 1 may be biocompatible. The term 'biocompatible' refers to a composition or structure comprising the composition, wherein the composition is compatible with living tissue or a living system by not being toxic, injurious, or physiologically reactive and not causing immunological rejection. The scaffold 1 may be biodegradable. The term 'biodegradable' refers to a composition or structure comprising the composition that will degrade or erode in vivo to form smaller chemical species.

The multi-layered structure 10 may comprise a first major surface 11 that is opposite a second major surface 12 as well as a side surface 13 that extends between the first and second major surfaces 11, 12. The multi-layered structure 10 may comprise at least an upper layer 40 (also referred to as "uppermost layer") positioned atop a bottom layer 30 (also referred to as "bottommost layer")—as discussed further herein. In some embodiments, the multi-layered structure 10 may further comprise one or more intermediate layers 50 positioned between the bottom layer 30 and the upper layer 40—as discussed further herein.

The multi-layered structure 10 of the scaffold 1 may comprise at least a first layer 100 and a second layer 200. In the non-limiting exemplified embodiment of FIG. 1, the multi-layered structure 10 scaffold 1 may comprise a first layer 100, a second layer 200, a third layer 300, a fourth layer 400, a fifth layer 500, and a sixth layer 600. In other embodiments, the multi-layered structure 10 may comprise a number of layers ranging from 2 to about 30 layers—including all integers and sub-ranges there-between. In other embodiments, the multi-layered structure 10 may comprise a number of layers ranging from 2 to about 14 layers—including all integers and sub-ranges there-between. In other embodiments, the multi-layered structure 10 may comprise more than 30 layers.

The first layer 100 may form the bottom layer 30 of the multi-layered structure 10. As discussed further herein, the upper layer 40 may be at least partially formed by the final layer of the multi-layered structure 10—whereby the "final layer" refers to highest numbered layer of the multi-layered structure 10.

In a non-limiting example, when a total of two (2) layers (i.e., a first layer 100 and a second layer 200) are used to form the multi-layered structure 10, the first layer 100 may form the bottom layer 30 and the second layer 200 may form the upper layer 40 because the second layer 200 is the final layer of the multi-layered structure 10 having two (2) layers.

In another non-limiting example that is demonstrated by FIG. 1, when a total of six (6) layers (i.e., a first layer 100, a second layer 200, a third layer 300, a fourth layer 400, a fifth layer 500, and a sixth layer 600) are used to form the multi-layered structure 10, the first layer 100 may form the bottom layer 30 and the sixth layer 600 may form the upper layer 40 because the sixth layer 600 is the final layer of the multi-layered structure 10 having six (6) layers.

When three or more layers are used to form the multi-layered structure 10, the layers other than the first layer 100 and the final layer may form the intermediate layers 50 of the multi-layered structure 10. In a non-limiting example, when a total of six (6) layers are used to form the multi-layered structure 10, the second layer 200, third layer 300, fourth layer 400, and fifth layer 500 may form the intermediate layers 50—whereby the intermediate layers 50 are positioned between the first and sixth layers 100, 600—as demonstrated by FIG. 1.

The second major surface 12 of the multi-layered structure 10 may form a bottom surface of the multi-layered structure 10 (i.e., the phrases "second major surface" and "bottom surface" may be used interchangeably). The first major surface 11 of the multi-layered structure 10 may form an upper surface of the multi-layered structure 10 (i.e., the phrases "first major surface" and "upper surface" may be used interchangeably).

The second major surface 12 may comprise at least a portion of the first layer 100 such that the first layer 100 may form at least a portion of the bottom surface 12 of the multi-layered structure 10. The first major surface 11 may comprise at least a portion of the final layer such that the final layer may form at least a portion of the upper surface 11 of the multi-layered structure 10. The side surface 13 may comprise at least a portion of the first layer 100, a portion of the final layer, and a portion of any intermediate layers disposed between the first and final layers.

As discussed in greater detail herein, each of the layers 100, 200 . . . , etc., that make up the multi-layered structure 10 may comprise a plurality fibers arranged in a substantially parallel array, whereby each fiber extends along an longitudinal axis that intersects opposing terminal ends of that fiber. Each fiber may have a fiber diameter $D_F$ as measured in a direction orthogonal to the longitudinal axis of the fiber. The fiber diameter $D_F$ may range from about 40 µm to about 300 µm—including all diameters and sub-ranges there-between.

For a single layer, the fiber diameter $D_F$ may remain substantially constant. In other embodiments, for a single layer, the fiber diameter $D_F$ may differ from fiber to fiber—as discussed further herein. In other embodiments, the fiber diameter $D_F$ of one layer may differ from the fiber diameter $D_F$ of a separate layer—as discussed further herein. In other embodiments, the fiber diameter $D_F$ may be substantially the same for multiple layers—as discussed further herein.

For any single layer, the longitudinal axis of each fiber may be substantially parallel to the longitudinal axis of the other fibers in the single layer. Each fiber may comprise an outer surface that is offset from the outer surface of an adjacent fiber in a single layer by an offset length $L_O$ that remains substantially constant as measured along the longitudinal axis of each fiber. The offset length $L_O$ may range from about 100 μm to about 500 μm—including all distances and sub-ranges there-between.

For a single layer, the offset length $L_O$ between all fibers may remain substantially constant. In other embodiments, for a single layer, the offset length $L_O$ may differ between two different sets of adjacent fibers—as discussed further herein. In other embodiments, the offset length $L_O$ between fibers for one layer may differ from offset length $L_O$ of a separate layer—as discussed further herein. In other embodiments, the offset length $L_O$ may be substantially the same for multiple layers—as discussed further herein.

For each single layer, a ratio may exist between the offset length $L_O$ and the fiber diameter $D_F$ that ranges from about 1.6:1.0 to about 12.5:1.0—including all ratios and sub-ranges there-between. In a preferred embodiment, the ratio may range from about 2.5:1 to about 10:1—including all ratios and sub-ranges there-between.

In one embodiment, the first layer 100 may comprise a plurality first fibers 110 that are arranged in a substantially parallel array, whereby each of the first fibers 110 extends along a first longitudinal axis A-A that intersects opposing terminal ends 115 of the first fiber 110. Each first fiber 110 may have a first fiber diameter $D_1$ as measured in a direction orthogonal to the first longitudinal axis A-A of the first fiber 110. The first diameter $D_1$ may be substantially equal to the fiber diameter $D_F$.

The first fibers 110 may be arranged such that the first longitudinal axis A-A of each first fiber 110 is substantially parallel to each other. Each of the first fibers 110 may comprise an outer surface 111. Within the first layer 100, the outer surface 111 of each first fiber 110 may be offset from the outer surface 111 of an adjacent first fiber 110 by a first offset length $L_1$. The first offset length $L_1$ as measured between two adjacent first fibers 110 may remain substantially constant as measured along the longitudinal axis A-A of each first fiber 110. The first offset length $L_1$ may be substantially equal to the offset length $L_O$.

In one embodiment, the second 200 may comprise a plurality second fibers 210 that are arranged in a substantially parallel array, whereby each of the second fibers 210 extends along a second longitudinal axis B-B that intersects opposing terminal ends 215 of the second fiber 210. Each second fiber 210 may have a second fiber diameter $D_2$ as measured in a direction orthogonal to the second longitudinal axis B-B of the second fiber 210. The second diameter $D_2$ may be substantially equal to the fiber diameter $D_F$.

The second fibers 210 may be arranged such that the second longitudinal axis B-B of each second fiber 210 is substantially parallel to each other. Each of the second fibers 210 may comprise an outer surface 211. Within the second layer 200, the outer surface 211 of each second fiber 210 may be offset from the outer surface 211 of an adjacent second fiber 210 by a second offset length $L_2$. The second offset length $L_2$, as measured between two adjacent second fibers 210, may remain substantially constant as measured along the longitudinal axis B-B of each second fiber 210. The second offset length $L_2$, may be substantially equal to the offset length $L_O$.

The fibers of a single layer may be arranged in a non-parallel relationship to the fibers of an adjacent layer. In other embodiments, the fibers of a single layer may be arranged in a parallel relationship to the fibers of another layer present in the multi-layered structure 10.

In a non-limiting example, the first fibers 110 of the first layer 100 may be disposed relative to the second fibers 210 of the second layer 200 such that the first longitudinal axis A-A of the first fibers 110 and the second longitudinal axis B-B of the second fibers 210 are in a non-parallel relationship. Specifically, a first intersection angle $\theta_1$ exists between the first and second longitudinal axis A-A, B-B of the first and second fibers 110, 220.

The first intersection angle $\theta_1$ may range from a value of greater than zero to less than 180°—preferably from at least about 1° to about 179°—including all angles and subranges there-between. In some embodiments, the first intersection angle $\theta_1$ may be 90° making the first and second fibers 110, 210 orthogonal to each other. In other embodiments, the first intersection angle $\theta_1$ may be oblique. In some embodiments, the oblique angle may be acute. In other embodiments, the oblique angle may be obtuse. In some embodiments, the first intersection angle $\theta_1$ may range from about 10° to about 90°—including all angles and sub-ranges there-between. In some embodiments, the first intersection angle $\theta_1$ may range from about 10° to about 45°—including all angles and sub-ranges there-between. In some embodiments, the first intersection angle $\theta_1$ may be about 10°, 15°, 20°, 25°, 30°, 35°, 40°, 45°, 50°, 55°, 60°, 65°, 70°, 75°, 80°, 85°, or about 90°—including all sub-ranges there-between.

With the first layer 100 and the second layer 200 being arranged in a non-parallel relationship, the combination of the first fibers 110 and the second fibers 210 form an intersecting pattern comprises a cross-hatch geometry having through-holes 20 that extend continuously between the plurality of first fibers 110 and the plurality of second fibers 210. The geometry of the through holes 20 of a combined first and second layer 100, 200 may be dictated generally by the first intersection angle $\theta_1$.

In a non-limiting example, when the first intersection angle $\theta_1$ is a right angle the through-holes 20 that exist through the combination of the first and second layers 100, 200 will be rectangular—whereby the through hole 20 may either be a square or a non-square rectangle. In a non-limiting example, when the first intersection angle $\theta_1$ oblique, the through holes 20 that exist through the combination of the first and second layers 100, 200 will be a non-rectangular parallelogram.

The dimensions of the through-hole 20 may be dictated by the first offset length $L_1$ of the first layer 100 and the second offset length $L_2$, of the second layer 200. For instance, the length (or width) of the through-hole 20 may be substantially equal to the first offset length $L_1$ and the width (or length) of the through-hole 20 may be substantially equal to the second offset length $L_2$.

According to some embodiments, when the first offset length $L_1$ of the first layer 100 is substantially equal to the second offset length $L_2$, of the second layer 200, the resulting through-hole 20 may either a rhombus or square (depending on the first intersection angle $\theta_1$. However, when the first offset length $L_1$ of the first layer 100 is not equal to the second offset length $L_2$, of the second layer 200, the resulting through-hole 20 may either be a non-square rectangle or an oblong parallelogram (depending on the first intersection angle $\theta_1$.

As discussed in greater detail herein, the presence of the through-hole 20 for a combined first and second layer 100, 200 provides a fluid pathway that extends throughout the multi-layered structure 10. As addressed further herein, the discussion with respect to the first layer 100 and second layer 200 above generally applies to any additional layers (300, 400, 500, 600, etc.) included in the multi-layered structure 10, except with regard to the differences specifically noted below.

Additionally, the intermediate layers 50 may comprise one or more of the second layer 200, third layer 300, fourth layer 400, fifth layer 500, sixth layer 600, etc. . . . layer before the final layer. Each of the intermediate layers 50 may comprise a plurality of the respective second fibers 110, third fibers 310, fourth fibers 410, fifth fibers 510, sixth fibers 610, etc.—whereby the foregoing each of the first fibers 110 also applies to the fibers of the intermediate layer 50.

Figure 6:
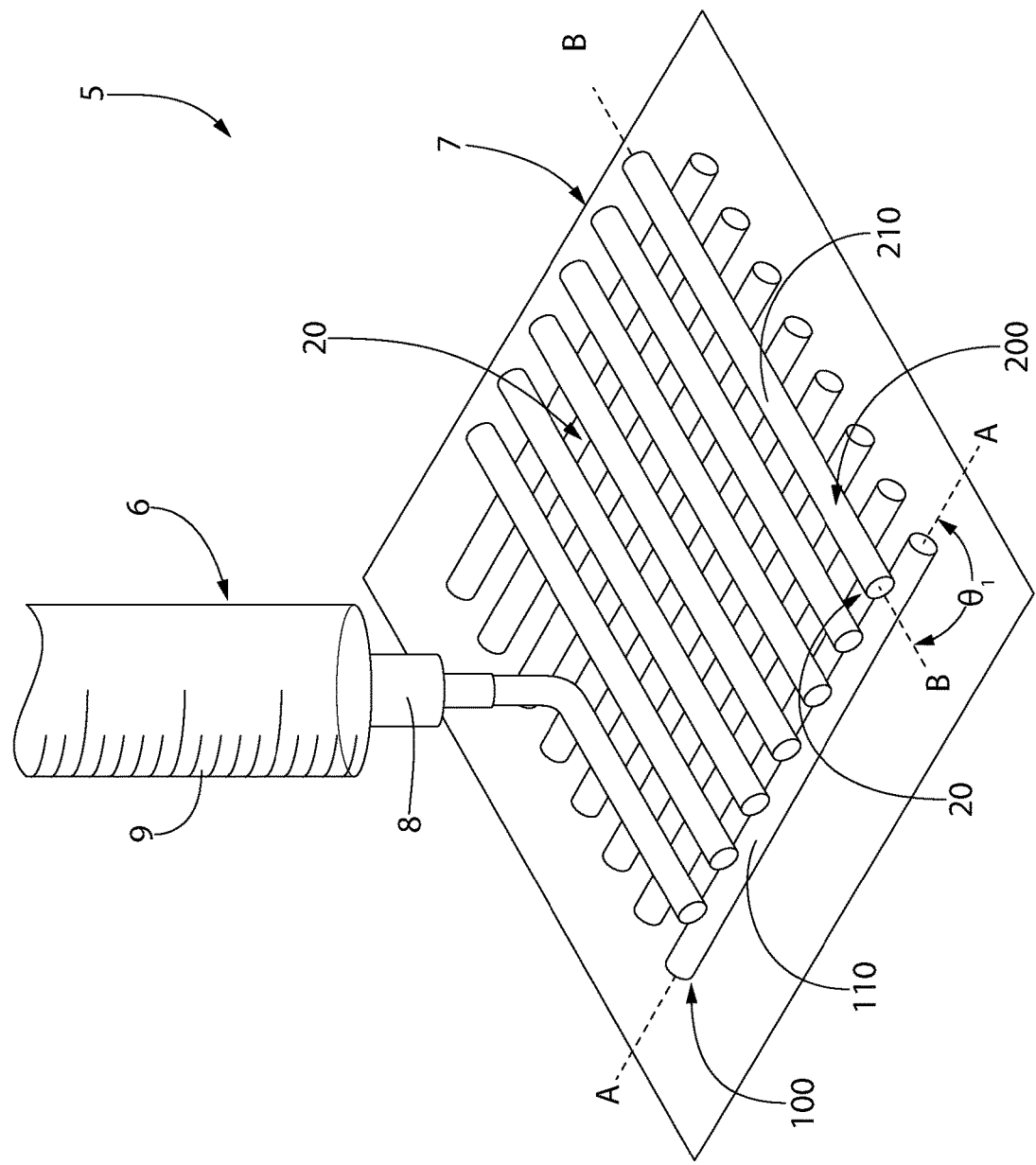
FIG. 6 is a perspective close-up view of a manufacturing process of the scaffold according to one embodiment of the present invention.

Referring now to FIG. 6, the multi-layered structure 10 of the present invention may be formed by 3D-printing a scaffold ink-composition (also referred to as an "ink-composition") in a wet-state. After printing, the wet-state ink-composition may be dried into a dry-state, thereby forming each of the first layer 100, second layer 200 . . . the final layer, of the multi-layered structure 10. The term "3D-printing" refers to three-dimensional printing techniques that use layering to build three-dimensional articles. Each of the first layer 100, second layer 200 . . . etc., to final layer may be formed by one or more continuous passes of a 3D-printer—as discussed further herein.

As discussed in greater detail herein, the ink-composition may generally comprise a blend of a first polymer and a second polymer. In some embodiments, the ink-composition may further comprise one or more additives. The phrase "wet-state" refers to the ink-composition further comprising a liquid carrier. The phrase "dry-state" refers to the ink-composition being substantially free of the liquid carrier. Knowing the amount of liquid carrier present in the ink-composition in the wet-state, the components present in the ink-composition in the dry-state can be used to calculate the corresponding amount of those components in the wet-state ink composition. For example, for a desired dry-state ink-composition that comprises about 50 wt, % of the first polymer, whereby that ink-composition is to be applied by 3D-printing in the wet-state with 30 wt. % of liquid carrier, the corresponding amount of the first polymer in the wet-state ink composition would be about 35 wt. % based on the total weight of the ink composition in the wet-state—i.e., (100 wt. %–30 wt. %)×50 wt. %=35 wt. % of the first polymer in the ink-composition in the wet-state.

Regarding the first polymer of the ink composition, such polymer may be biocompatible. The first polymer may be biodegradable. The first polymer may be a peptide conjugate polymer. The peptide conjugate polymer may have the structure forth in Formula I:

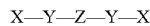  Formula I

The Z-component is a biocompatible polymer block. The Y-component is a linking group that may be derived from a linker compound. The X-component is a biologically active peptide block. Covalent bonds are created between the biologically active peptide and the linker moiety as well as between the linker moiety and the biocompatible polymer block.

In other embodiments, the peptide conjugate polymer may be a branched polymer having at least three branches, whereby the terminal groups of each branch comprise a X-component. In other embodiments, the peptide conjugate polymer may be a substantially linear polymer having the structure of Formula I, whereby at least one X-component is directly pendant off the central region of the biocompatible polymer backbone of the Z-component.

The biocompatible polymer backbone of Z-component may be a polyester block. A non-limiting example of biocompatible polyester may be a polyester derived from a cyclic-ester. Non-limiting examples of cyclic-ester include lactones having the Formula II:

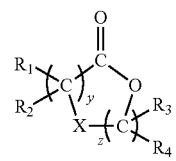

Formula II where X=nil, —O—, or —O—C═O; wherein, Z=1-3; wherein Y=1-4; wherein $R_1$-$R_4$=H—, —$CH_3$, $C_2$-$C_{16}$ alkyl group, —$C(CH_3)$, or $HOCH_2$, and where all R's are independent on each y or z carbon unit and independent of each other. In other embodiments, the lactone has the Formula III:

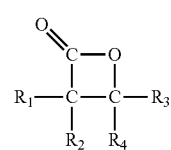

Formula III where $R_1$-$R_4$=H—, —$CH_3$, $C_2$-$C_{16}$ alkyl group, or $HOCH_2$—, and where all R's are independent of each other.

Non-limiting examples of the lactones described above include, but not limited to, caprolactone, t-butyl caprolactone, zeta-enantholactone, deltavalerolactones, the monoalkyl-delta-valerolactones, e.g, the monomethyl-, monoethyl-, monohexyl-deltavalerolactones, and the like; the nonalkyl, dialkyl, and trialkyl-epsilon-caprolactones, e.g. the monomethyl-, monoethyl-, monohexyl-, dimethyl-, di-n-propyl, di-n-hexyl-, trimethyl-, triethyl-, tri-n-epsilon-caprolactones, 5-nonyl-oxepan-2-one, 4,4,6- or 4,6,6-trimethyl-oxepan-2-one, 5-hydroxymethyl-oxepan-2-one, and the like; beta-lactones, e.g., beta-propiolactone, beta-butyrolactone gamma-lactones, e.g., gammabutyrolactone or pivalolactone, dilactones, e.g. lactide, dilactides, glycolides, e.g., tetramethyl glycolides, and the like, ketodioxanones, e.g.

1,4-dioxan-2-one, 1,5-dioxepan-2-one, and the like. The lactones can consist of the optically pure isomers or two or more optically different isomers or can consist of mixtures of isomers.

In a preferred embodiment, the lactone may be ε-caprolactone and its derivatives and other seven membered ring lactones—whereby ε-caprolactone has the formula:

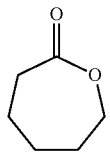

In one aspect of the present invention, other monomers may be polymerized with the lactones to comprise the first monomer, such as, for example, one or more compounds which can be polymerized or copolymerized to form aliphatic polyesters or polyester amides or other condensation polymers. Examples of such monomers may include substituted or unsubstituted $C_2$-$C_8$ diols, e.g., ethylene glycol, diethylene glycol, butanediol, neopentyl glycol, and hexanediol.

In other embodiments, the cyclic-ester may be polymerized with a previously formed polyester that is the reaction product of one of the previously discussed $C_2$-$C_8$ diols and a dicarboxylic acids, such as but not limited to, succinic, glutaric or adipic acid; terephthalic acid.

In some embodiments, the Z-component may be a ethylene glycol initiated poly(caprolactone) ("PCL") polymer comprising terminal hydroxyl groups having the formula:

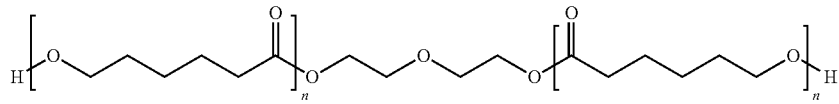

Whereby n is an integer ranging from about 40 to about 80—including all integers and sub-ranges there-between. In some embodiments, the n value will result in the PCL polymer having a weight-average molecular weight ("MW") ranging from about 10,000 g/mol to about 18,000 g/mol, preferably about 13,000 g/mol to about 16,000 g/mol, including all molecular weights and sub-ranges there-between. In alternative embodiments, the weight-average molecular weight of the Z-component may be up to about 45,000 g/mol.

In other embodiments, the Z-component may be poly(caprolactone) ("PCL") polymer having hydroxyl groups (or other functional groups) present on the backbone of the polymer that are in addition to the terminal groups.

The first polymer may be present in the ink-composition in the dry-state in an amount ranging from about 35% w/v to about 100% w/v—including all amounts and sub-ranges there-between. In some embodiments, the first polymer may be present in the ink-composition in the dry-state in an amount ranging from about 35% w/v to about 65% w/v—including all amounts and sub-ranges there-between. In a preferred embodiment, the first polymer may be present in the ink-composition in the dry-state in an amount ranging from about 35% w/v to about 60% w/v—including all amounts and sub-ranges there-between.

The linking group that makes up the Y-component may be formed from a linker compound comprising a maleimide group as well as a functional group capable of reacting with the terminal functional groups present on the backbone polymer of the Z-component. In a non-limiting example, the linker compound comprises a maleimide group as well as a hydroxyl-reactive group (e.g., carboxylic acid, isocyanate group, and the like). The maleimide-containing linker compound may comprise an aromatic group, an aliphatic chain, and combinations thereof.

In a non-limiting example, the linker moiety comprises p-maleimide phenyl isocyanate ("PMPI") having the formula:

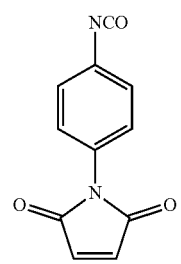

Whereby the isocyanate groups present on the PMPI reacts with the terminal groups present on the polymer backbone of the Y-component. In a non-limiting embodiment, the isocyanate groups present on the PMPI react with the hydroxyl terminal groups present on the poly(caprolactone) polymer backbone so form an intermediate polymer comprising maleimide-terminated poly(caprolactone) having two urethane linkages bridging the maleimide groups to the poly(caprolactone) backbone.

The X-component is a biologically active peptide. The biologically active peptide that makes up the X-component may be formed from a peptide compound comprising a functional group capable of reacting with the maleimide functional groups present on the intermediate polymer formed of the Z-component and Y component. In a non-limiting example, the peptide compound may comprise a thiol group. In other embodiments, the peptide compound may be amine-functionalized. In a non-limiting embodiment, the thiol group present on the peptide compound reacts with the terminal maleimide groups present on the intermediate polymer so as to form a peptide-terminated peptide-polymer conjugate having two urethane linkages bridged together by a poly(caprolactone) backbone.

In a non-limiting embodiment, the biologically active peptide is formed from a thiol functional peptide. Thiol functional peptide may be a cysteine containing peptide. In a non-limiting embodiment, the peptide may include hyaluronic binding, mineralizing, and cell adhesion peptides. The amino acid sequence of each peptide may be tailorable and can therefore be designed for a desired application. In a non-limiting embodiment, the X-component of the present invention may include peptides having about 5 to about 30 amino acids in length.

In a non-limiting example, the peptide may be selected from CGGGAAAEEE and/or CGGGRYPISRPRKR as being suitable to promote mineralization and hyaluronic acid binding.

As discussed, the ink-composition may further comprise a second polymer. The second polymer may be biocompatible. The second polymer may be biodegradable. The second polymer may be a polyester polymer. The polyester polymer may be derived from one or more of the cyclic-esters disclosed as being suitable for the Z-component. In a non-limiting embodiment, the second polymer may be poly(caprolactone) that is substantially free of peptide conjugation. The second polymer may be substantially free of peptide groups. The second polymer may be a poly(caprolactone) homopolymer.

The second polymer may have a weight average molecular weight Mw ranging from about 10,000 g/mol to about 400,000 g/mol—including all weight average molecular weights Mw and subranges there-between.

The second polymer may be present in the ink-composition in the dry-state in an amount ranging from about 0% w/v to about 65% w/v—including all amounts and sub-ranges there-between. In some embodiments, the second polymer may be present in the ink-composition in the dry-state in an amount ranging from about 35% w/v to about 65% w/v—including all amounts and sub-ranges there-between. In some embodiments, the second polymer may be present in the ink-composition in the dry-state in an amount ranging from about 40% w/v to about 65% w/v—including all amounts and sub-ranges there-between.

The first polymer and the second polymer may be physically blended together in the ink-composition. The first polymer and the second polymer may be present together in weight ratio ranging from about 1:2 to about 5:1—including all weight ratios and sub-ranges there-between. In other embodiments, the first polymer and the second polymer may be present together in weight ratio ranging from about 1:2 to about 3:1—including all weight ratios and sub-ranges there-between.

In the wet-state, the ink-composition may comprise a liquid carrier. The liquid carrier may be a solvent. Non-limiting examples of solvent include volatile solvent (as measured at room temperature). Volatile solvent may be selected from one or more of water; dichloromethane ("DCM"); hexafluoro-1-propanol ("HFIP"); methanol; ethanol; propanol; isopropyl alcohol; acetone; isobutene; pentane; hexane; dimethyl ether; methyl ethyl ketone; diethyl ether; 1,1, difluoroethane; 1,1,1,2 tetrafluorethane; 1,1,1,2,3,3,3-heptafluoropropane; 1,1,1,3,3,3 hexafluoropropane; ethyl acetate; or combinations thereof. In another embodiment, the volatile solvent system can include iso-amyl acetate, denatured alcohol, chlorobutanol, turpentine, cytopentasiloxane, cyclomethicone, or combinations thereof. In some embodiments, the volatile solvent may be selected from methylene chloride; acetic acid; ethyl acetoacetate; dimethylsulfoxide; n-methyl pyrrolidone; 2-amino-2-methyl-1-propanol; 1-amino-2-propanol; 2-dimethylamino-2-methyl-1-propanol; N,N-diethylethanolamine; N-methyldiethanolamine; N,N-dimethylethanolamine; triethanolamine; 2-aminoethanol; 1-[bis[3-(dimethylamino)propyl]amino]-2-propanol; 3-amino-1-propanol; 2-(2-aminoethylamino)ethanol; tris(hydroxymethyl)aminomethane; 2-amino-2-ethyl-1,3-propanediol; 2-amino-2-methyl-1,3-propanediol; diethanolamine; 1,3-bis(dimethylamino)-2-propanol; and combinations thereof.

The liquid carrier may be present in the ink-composition in the wet-state in an amount ranging from about 5% w/v to about 95% w/v—including all amounts and sub-ranges there-between.

Referring again to FIG. 6, the 3D-printing process may comprise a printing system 5 that includes a 3D-printer 6 and a support substrate 7 on which the 3D-printing occurs. The 3D-printer 6 may comprise at least one reservoir comprising the ink-composition as well as a printing head 8 that ejects the ink-composition from the reservoir 9 onto the support substrate 7 to form the first layer 100. Subsequent layers may be applied atop the first layer 100. In the non-limiting embodiment of FIG. 6, the second layer 200 is printed atop the first layer 100, which has been printed atop the support substrate 7. In a non-limiting example, the substrate 7 may be glass.

The printing head 8 may be in the form of an adjustable nozzle that directs the wet-state ink-composition from the reservoir 9 in a control manner, thereby controlling fiber diameter $D_F$. The 3D-printing process may use pneumatic extrusion to direct (e.g., extrude) the wet-state ink composition through a needle nozzle to form each fiber of each layer.

The printer 6 is mounted onto at least a moveable three-dimensional support axis (X, Y, Z) allowing the printing head 8 to achieve precise placement within the printing system 5 during printing. In combination with printing head 8 placement/movement (i.e., printing speed), the 3D-printing process may also use extrusion speed and/or needle gauge to further provide precise control over fiber diameter $D_F$, offset length $L_O$ between adjacent fibers of a single layer, as well as the orientation of fibers within one layer relative to the orientation of fiber within an adjacent layer. The precise placement of each fiber within each layer provides the ability to fine tune the porosity of the resulting multi-layered structure 10, thereby fine tuning the porosity of the scaffold 1.

Once the wet-state ink-composition applied by the printing head 8, the liquid carrier may evaporate, thereby transforming the wet-state ink composition into the dry-state ink-composition. The dry-state ink composition may form the multi-layered structure 10 of the present invention. Evaporation of the liquid carrier from the wet-state ink composition may be performed under atmospheric conditions—i.e., 1 atm and room temperature (about 70° F.). In other embodiments, one or more heaters may be used to help accelerate the evaporation of the liquid carrier from the wet-state ink composition.

The wet-state ink composition may within the reservoir 9 at room temperature, whereby 3D-printing of the wet-state ink composition is performed at room temperature. In other embodiments, the wet-state ink composition may be heated within the reservoir 9 to an elevated temperature that is above room temperature, whereby 3D-printing of the wet-state ink composition is performed at the elevated temperature. In a non-limiting embodiment, the wet-state ink composition may be heated within the reservoir 9 and 3D-printed at an elevated temperature ranging from about 25° C. to about 200° C.—including all temperatures and sub-ranges there-between. In a preferred embodiment, the wet-state ink composition may be within the reservoir 9 and 3D-printed at room temperature.

Once the ink composition is printed to form the multi-layered structure 10, one or more coatings may be applied to the multi-layered structure 10 to form the scaffold 1 of the present invention. In other embodiments, the peptide-conjugation of the first polymer presents the functionality on the surface of the multi-layered structure 10 without the need of additional functionalization steps, thereby resulting in the 3D-printed multi-layered structure 10 being suitable as the scaffold 1 of the present invention without further need of surface modifying chemistries. Additionally, by varying the concentration of conjugate added, the local concentration of peptides presented on the surface of each layer within a multi-layered structure 10 and resulting scaffold 1 can be controlled.

Additionally, by varying the layout of each layer—whether it be fiber diameter $D_F$, offset length $L_O$, relative fiber orientation relative to adjacent layers via the intersection angle $\theta_1, \theta_2 \ldots$ etc. the resulting multi-layered structure 10 may be composed of any number of peptide-modified polymer ink compositions, each having different peptide sequences and varying spatial concentrations, whereby changing the orientation, distribution, and diameter of the printed fibers allows for regional control of physical properties across the scaffold.

Additionally, the printing system 5 may comprise two or more 3D-printers 6 or a single 3D-printer 6 having two or more reservoirs 9, whereby each reservoir contains a different ink composition. In a non-limiting example, a first reservoir 9 may comprise a first ink composition having a first concentration of a first polymer and a second polymer and a second reservoir 9 may comprise a second ink composition having a second concentration of the first polymer and the second polymer, whereby the first and second polymers of the first and second ink compositions are the same chemically, but the first and second concentrations of the first and second ink compositions are not equal.

In another non-limiting example, a first reservoir 9 may comprise a first ink composition having a first polymer and a second polymer and a second reservoir 9 may comprise a second ink composition having a first polymer and a second polymer, whereby the first polymer of the first ink composition and the first polymer of the second ink composition are chemically distinct. In such non-limiting example, the concentrations of the first polymer in each of the first ink composition and second ink composition may be the same or different.

In a non-limiting example, the phrase "chemically distinct" may refer to the first polymer having different peptide groups present in the X-component of the first polymer. In a non-limiting example, the phrase "chemically distinct" may refer to the first polymer having different linker chemistries in the Y-component of the first polymer. In a non-limiting example, the phrase "chemically distinct" may refer to the first polymer having different polymer backbone chemistry in the Z-component of the first polymer. In a non-limiting example, the phrase "chemically distinct" may refer to the first polymer having different molecular weights within the Z-component of the first polymer. In a non-limiting example, the phrase "chemically distinct" may refer to varying amounts of the X-component bonded to polymer backbone of the Z-component—e.g., only two terminal peptide groups vs. three or more peptide groups present along the polymer back bone of the Z-component of the first polymer.

According to the present invention, 3D-printing ink compositions comprising first polymer—as well as second polymer—allows for the fabrication of scaffolds for tissue engineering that resemble native tissue organization to guide functional tissue regeneration. The resulting scaffolds 1 are suitable as biomaterials for tissue engineering that can promote tissue regeneration and restore or replace diseased or damaged tissues. The porous, biodegradable scaffolds 1 are used to provide mechanical support during the early stages of regeneration while also allowing for cell infiltration and nutrient diffusion. Additionally, targeted control over placement of peptide conjugation within each layer 100, 200, etc. . . . results in the scaffold 1 having a hierarchical structure that combines multiple components together to perform functions that could not be achieved by each component alone. Therefore, scaffolds 1 can be designed to match gradients in biochemical and biophysical properties that exist in numerous tissues, including those of the musculoskeletal, cardiovascular, and neural systems In a non-limiting embodiment, articular cartilage is a musculoskeletal tissue that covers the ends of long bones to facilitate low-friction movement while distributing mechanical loads. This tissue exhibits depth-dependent gradients in structure, cell type, and ECM components, leading to anisotropic mechanical properties that are critical for biomechanical function. Cartilage serves as just one example of a complex tissue that exhibits essential intrinsic gradients in structure and function that provides a guiding inspiration for the design of new biomaterials.

Figure 2:
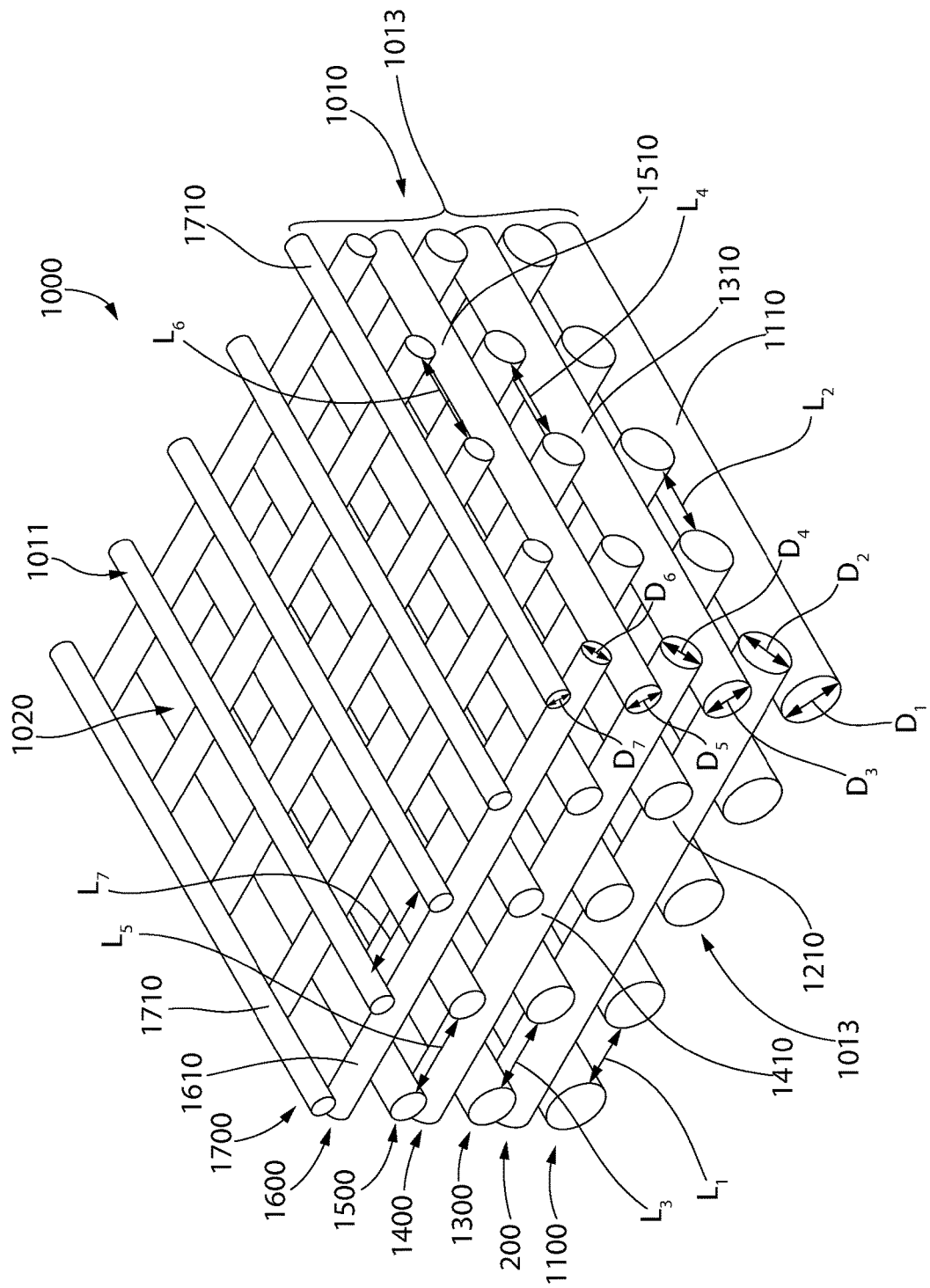
FIG. 2 is a perspective close-up view of a scaffold according to one embodiment of the present invention.

Referring now to FIG. 2, a non-limiting example will be provided for a scaffold 1000 having hierarchical structure that may be designed to match gradients of biochemical and biophysical properties that exist in tissues. The scaffold 1000 is similar to the scaffold 1 except as described herein below. The description of the scaffold 1 above generally applies to the scaffold 1000 described below except with regard to the differences specifically noted below. A similar numbering scheme will be used for the scaffold 1000 as with the scaffold 1, except that the 1000-series of numbers will be used.

The scaffold 1000 may comprise a multi-layered structure 1010 having at least a first layer 1100 and a second layer 1200. The first fibers 1110 of the first layer 1100 may have a first fiber diameter $D_1$ and the second fibers 1210 of the second layer 1200 may have a second fiber diameter $D_2$—whereby the first and second fiber diameters $D_1, D_2$, are not equal. The first fiber diameter $D_1$ may be substantially constant within the first layer 1100. The second fiber diameter $D_2$, may be substantially constant within the second layer 1200.

Additionally, the first fibers 1110 of the first layer 1100 may be offset from each other by a first offset length $L_1$ and the second fibers 1210 of the second layer 1200 may be offset from each other by a second offset length $L_2$—whereby the first and second offset lengths $L_1, L_2$ are not equal. The offset length $L_1$ may be substantially constant within the first layer 1100. The second offset length $L_2$ may be substantially constant within the second layer 1200.

The first fibers 1110 and the second fibers 1210 may overlap at a plurality of intersection points, whereby the plurality of intersection points across multiple layers 1100, 1200, 1300, 1400, 1500, 1600, etc., overlap such that the through holes 1020 extend continuously from the first major surface 1011 to the second major surface 1012 of the multi-layered structure 1010. In other embodiments, the first fibers 1110 and the second fibers 1210 may overlap at a first plurality of intersection points, and the second fibers 1210 and third fibers 1310 may overlap at a plurality of second intersection points, whereby the first and second plurality of intersection points do not overlap (not pictured in FIG. 2).

Figure 3:
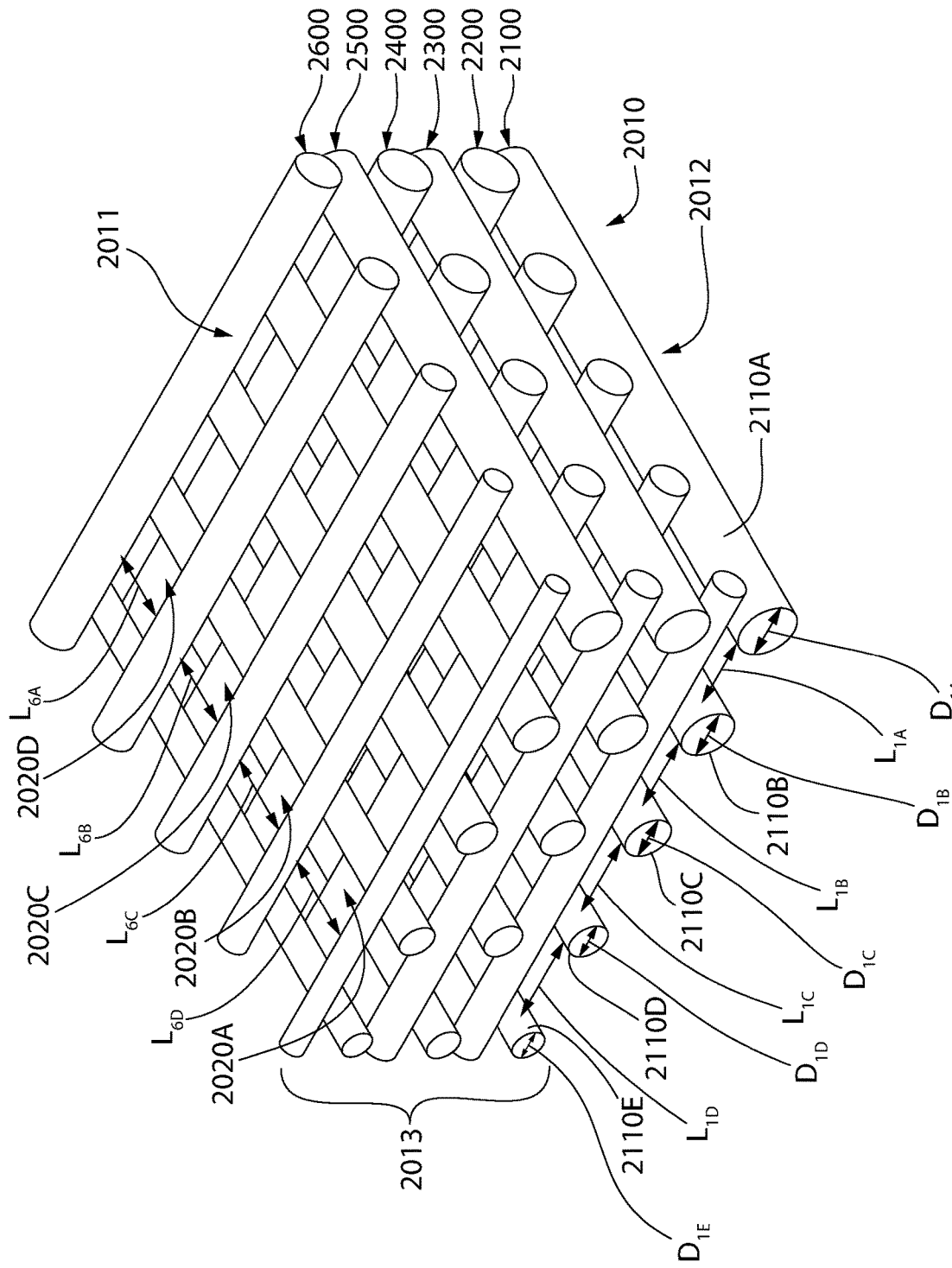
FIG. 3 is a perspective close-up view of a scaffold according to one embodiment of the present invention.

Referring now to FIG. 3, a non-limiting example will be provided for a scaffold 2000 having hierarchical structure that may be designed to match gradients of biochemical and biophysical properties that exist in tissues. The scaffold 2000 is similar to the scaffolds 1 and 1000 except as described herein below. The description of the scaffold 1 and 1000 above generally applies to the scaffold 2000 described below except with regard to the differences specifically noted below. A similar numbering scheme will be used for the scaffold 2000 as with the scaffold 1, except that the 2000-series of numbers will be used.

The scaffold 1000 may comprise a multi-layered structure 2010 having at least a first layer 2100 and a second layer 2200. The first layer 2100 may comprise a first set of fibers 2110A, 2110B, 2110C, 2110D, 2110E that each have their own first fiber diameter $D_{1A} D_{1B} D_{1C} D_{1D} D_{1E}$ . . . etc. The first fiber diameter $D_{1A} D_{1B} D_{1C} D_{1D} D_{1E}$ . . . etc. of each of the first fibers 2110A, 2110B, 2110C, 2110E, 2110E may vary within the first layer 2100. The second layer 2200 may also comprise a second set of fibers that each have their own second fiber diameter, whereby the second fiber diameter of each of the second fibers may vary within the first layer 2100. In some embodiments, at least one of the first fibers 2110A may be equal to at least one of the second fibers.

The first set of fibers 2110A, 2110B, 2110C, 2110D, 2110E, etc. may be arranged such that the first fiber diameter $D_{1A}, D_{1B}, D_{1C}, D_{1D}, D_{1E}$ . . . etc. increase in size forming an enlarging array of first fibers 2110A, 2110B, 2110C, 2110D, 2110E, etc. when moving in a single direction across the first layer 2100. In such embodiments, there may be a corresponding decrease in size of the offset length $L_{1A}, L_{1B}, L_{1C}, L_{1D}, L_{1E}$ . . . etc. between adjacent first fibers 2110A, 2110B, 2110C, 2110D, 2110E, etc. such that the dimension of through holes 2020A, 2020B, 2020C, 2020D, etc. decrease in size when moving along the single direction across the first layer 2100.

Each of the second layer 2200, third layer 2300, fourth layer 2400, fifth layer 2500, sixth layer 2600, etc., may also exhibit the same fiber diameter and offset length relationship as the first layer 2100 of this embodiment.

Figure 4A:
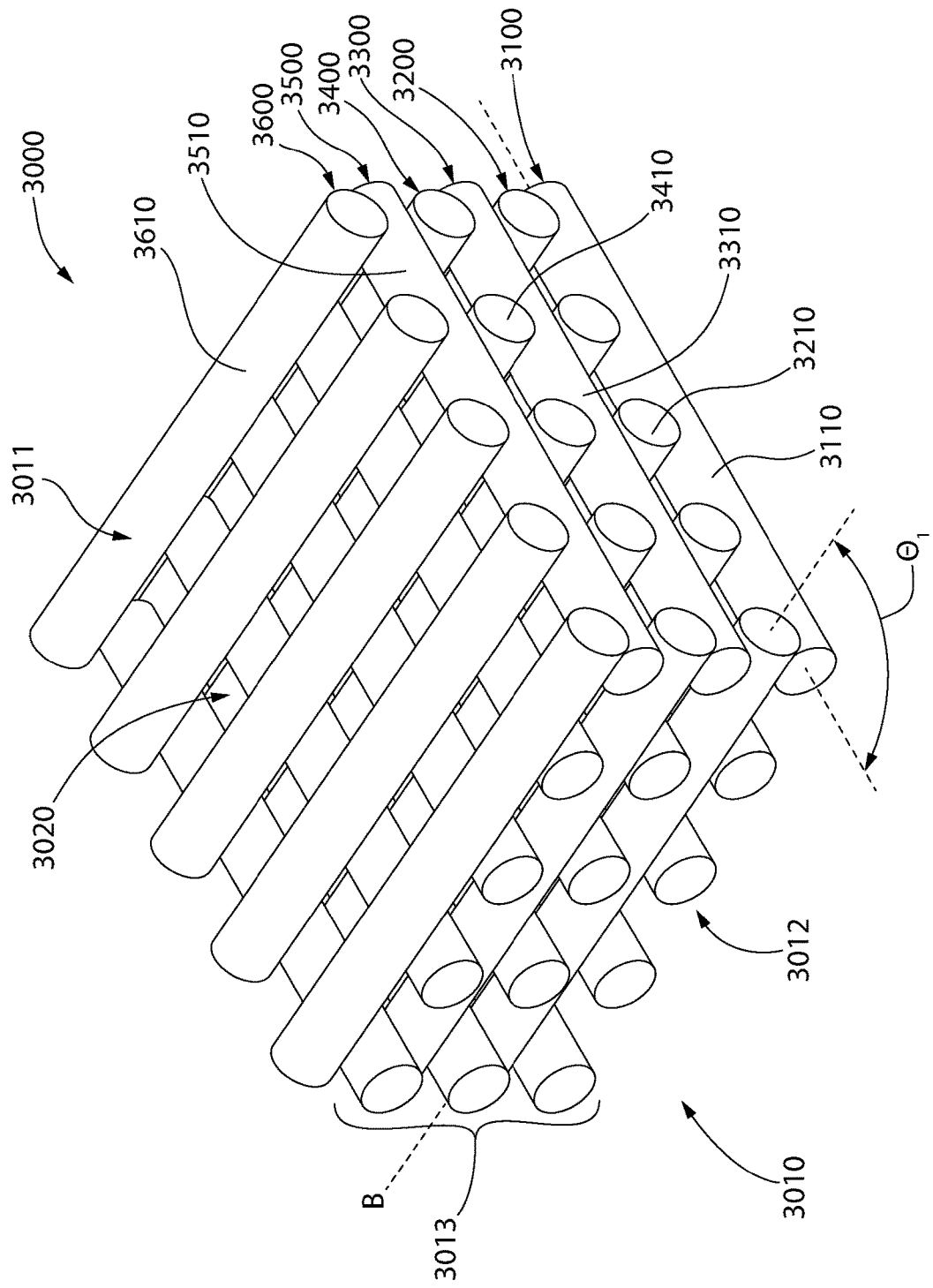
FIG. 4A is a perspective close-up view of a scaffold according to one embodiment of the present invention.
Figure 4B:
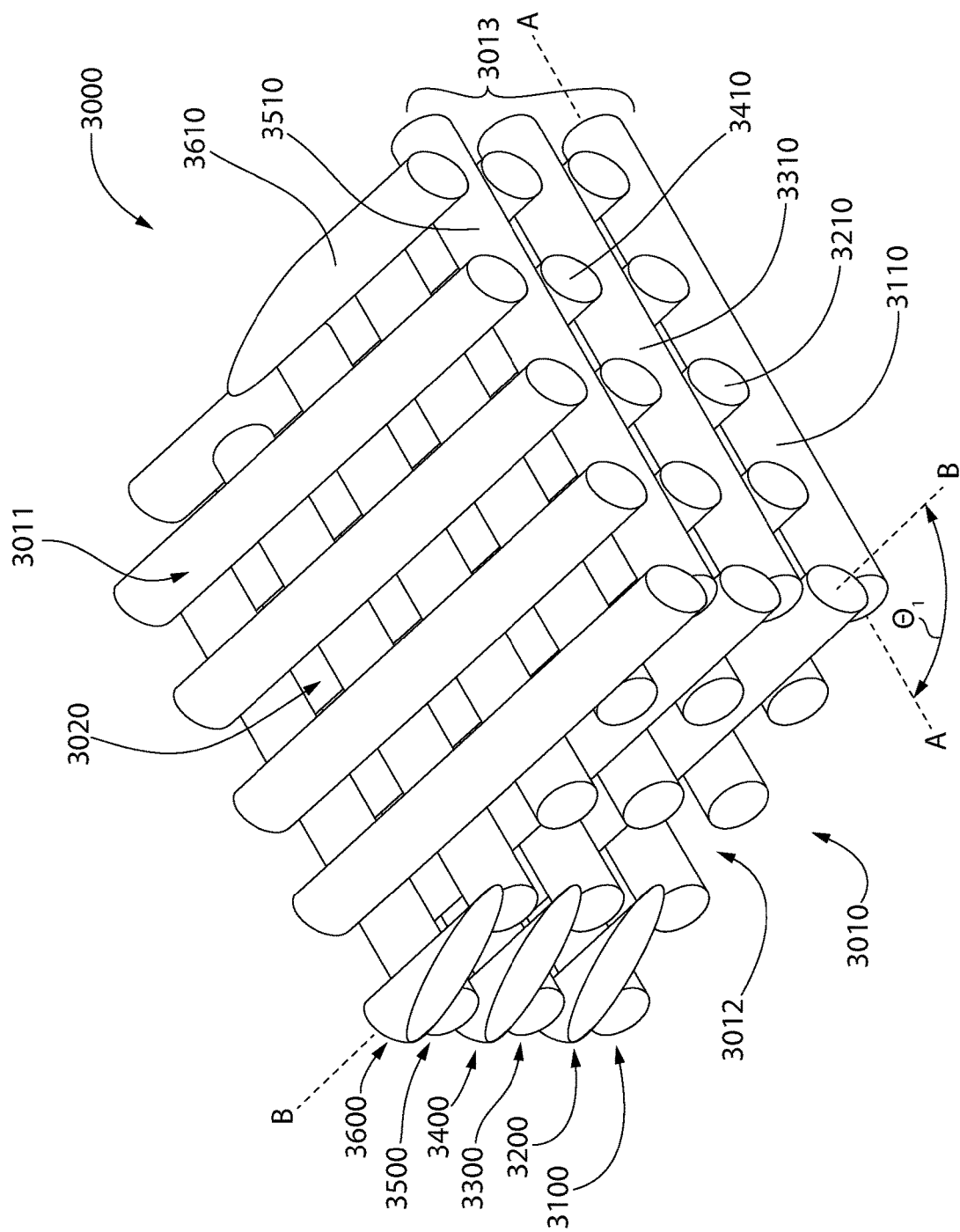
FIG. 4B is a perspective close-up view of a scaffold according to one embodiment of the present invention.
Figure 4C:
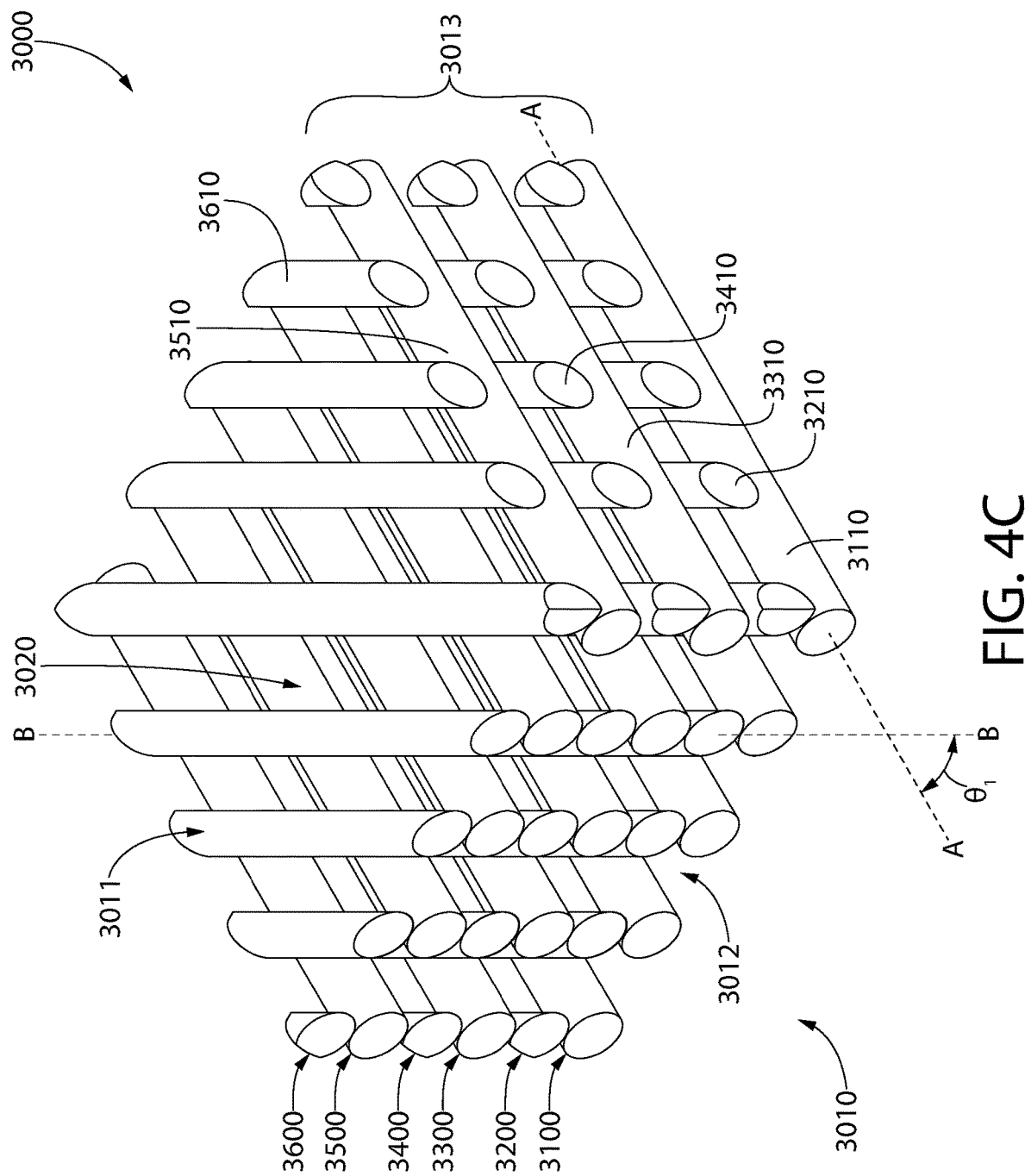
FIG. 4C is a perspective close-up view of a scaffold according to one embodiment of the present invention.

Referring now to FIG. 4A-4C, a non-limiting example will be provided for a scaffold 3000 having hierarchical structure that may be designed to match gradients of biochemical and biophysical properties that exist in tissues. The scaffold 3000 is similar to the scaffolds 1, 1000, 2000 except as described herein below. The description of the scaffold 1 above generally applies to the scaffold 3000 described below except with regard to the differences specifically noted below. A similar numbering scheme will be used for the scaffold 3000 as with the scaffold 1, except that the 3000-series of numbers will be used.

The scaffold 3000 may comprise a multi-layered structure 3010 having at least a first layer 3100 and a second layer 3200. The first layer 2100 may comprise first fibers 3110 and the second layer 2200 may comprise second fibers 3210. The first fibers 3110 of the first layer 3100 may be disposed relative to the second fibers 3210 of the second layer 3200 such that the first longitudinal axis A-A of the first fibers 3110 and the second longitudinal axis B-B of the second fibers 3210 are in a non-parallel relationship. Specifically, a first intersection angle $\theta_1$ exists between the first and second longitudinal axis A-A, B-B of the first and second fibers 3110, 3220.

The first intersection angle $\theta_1$ may range from a value of greater than zero to less than 180°—preferably from at least about 1° to about 89°—including all angles and subranges there-between. In some embodiments, the first intersection angle $\theta_1$ may be from about 10° to about 45°—including all angles and sub-ranges there-between. In some embodiments, the first intersection angle $\theta_1$ may be about 10°, 15°, 20°, 25°, 30°, 35°, 40°, 45°, 50°, 55°, 60°, 65°, 70°, 75°, 80°, 85°, or about 90°—including all sub-ranges there-between.

Figure 5:
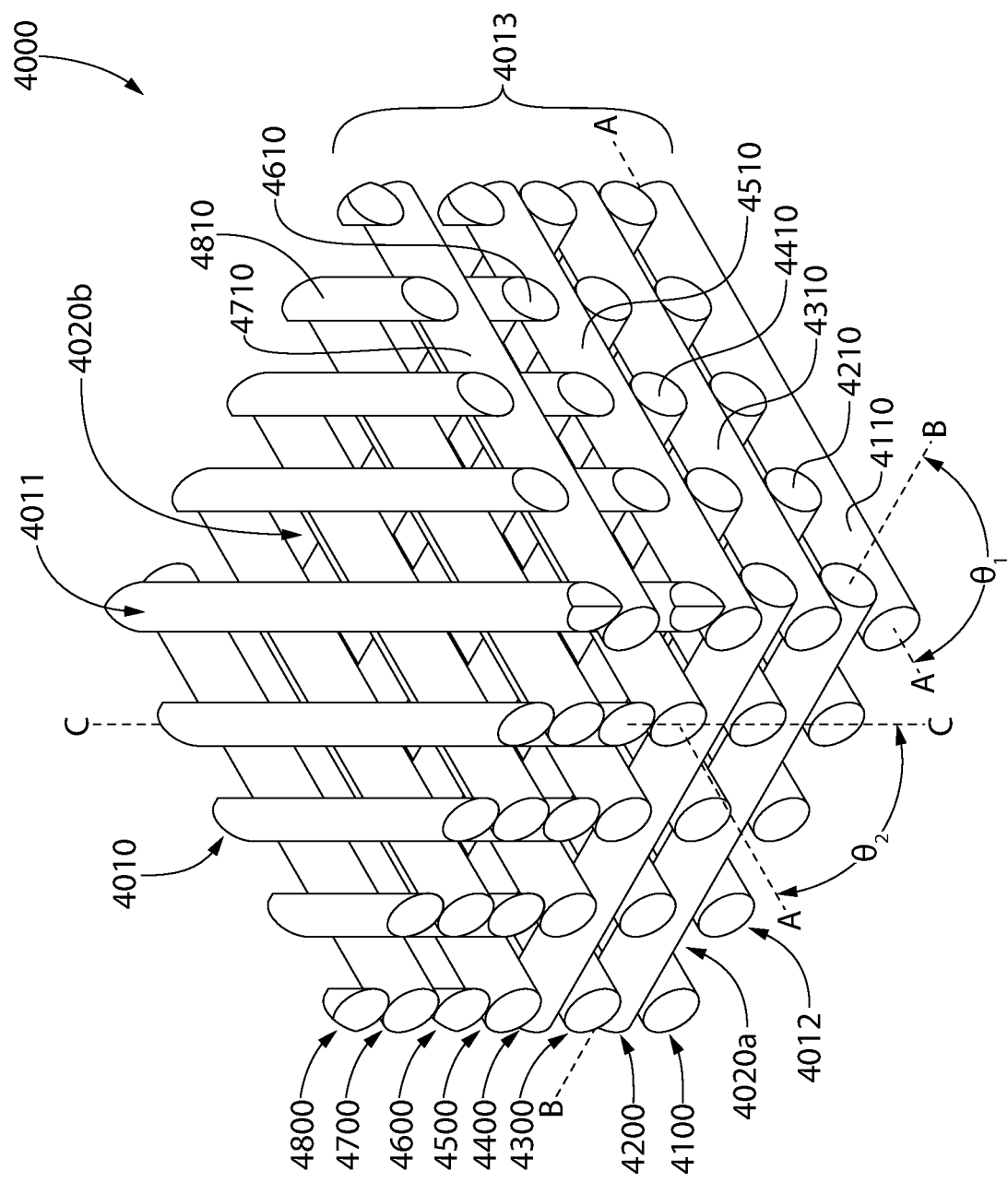
FIG. 5 is a perspective close-up view of a scaffold according to one embodiment of the present invention.

According to this embodiment, the through holes 2020 form non-rectangular parallelograms Referring now to FIG. 5, a non-limiting example will be provided for a scaffold 4000 having hierarchical structure that may be designed to match gradients of biochemical and biophysical properties that exist in tissues. The scaffold 4000 is similar to the scaffolds 1, 1000, 2000, and 3000 except as described herein below. The description of the scaffold 1, 1000, 2000, and 3000 above generally applies to the scaffold 4000 described below except with regard to the differences specifically noted below. A similar numbering scheme will be used for the scaffold 4000 as with the scaffold 1, except that the 4000-series of numbers will be used.

The scaffold 4000 may comprise a multi-layered structure 4010 having at least a first layer 4100, a second layer 4200, and a third layer 4600. The first fibers 4110 of the first layer 4100 may be disposed relative to the second fibers 4210 of the second layer 4200 such that the first longitudinal axis A-A of the first fibers 4110 and the second longitudinal axis B-B of the second fibers 4210 intersect at a first intersection angle $\theta_1$. The first fibers 4110 of the first layer 4100 may be disposed relative to the third fibers 4610 of the third layer 4600 such that the first longitudinal axis A-A of the first fibers 4110 and the third longitudinal axis C-C of the third fibers 4610 intersect at a second intersection angle $\theta_1$. According to this embodiment, the first and second intersection angles $\theta_1$, $\theta_2$, may be selected from any value that is of greater than zero to less than 180°—preferably from at least about 1° to about 90°—including all angles and sub-ranges there-between—so long as the first intersection angle $\theta_1$ and the second intersection angle $\theta_1$ are not equal.

According to this embodiment, the first fibers 4110 and the second fibers 4210 may overlap at a plurality of first intersect points, and the first fibers 1210 and third fibers 4610 may overlap at a plurality of second intersection points, whereby the first and second plurality of intersection points do not overlap. According to this embodiment, at least a first through hole 4020a is formed by the overlap of the first fibers 4110 and the second fibers 4210 and a second through hole 4020b is formed by the overlap of the first fibers 4110 and the third fibers 4610—whereby the first and second through holes 4020a, 4020b have different geometry (e.g., square vs. rhombus).

What is claimed is:

1. An implantable scaffold comprising a peptide-polymer conjugate, the peptide-polymer conjugate comprising:
    a biologically active peptide;
    a linker; and
    a biocompatible polymer,
    wherein the linker comprises a maleimide functionalized compound and at least one of a hydroxyl-reactive group, an aromatic group, or an aliphatic chain.

2. The implantable scaffold according to claim 1, wherein the biocompatible polymer is a polyester.

3. The implantable scaffold according to claim 2, wherein the polyester comprises a cyclic ester.

4. The implantable scaffold according to claim 3, wherein the cyclic ester is a lactone.

5. The implantable scaffold according to claim 4, wherein the lactone is selected from: caprolactone, t-butyl caprolactone, zeta-enantholactone, deltavalerolactones, monoalkyl-delta-valerolactones, nonalkyl-epsilon-caprolactones, dialkyl-epsilon-caprolactones, trialkyl-epsilon-caprolactones, monomethyl-epsilon-caprolactones, monoethyl-epsilon-caprolactones, monohexyl-epsilon-caprolactones, beta-lactones, gamma-lactones, dilactones, and a combination of two or more thereof.

6. The implantable scaffold according to claim 5, comprising a poly(caprolactone) having a molecular weight ranging from about 10,000 to about 18,000 g/mol.

7. The implantable scaffold according to claim 1, further comprising a high molecular weight polymer blended with the peptide-polymer conjugate.

8. The implantable scaffold according to claim 1, wherein the maleimide functionalized compound comprises an isocyanate group.

9. The implantable scaffold according to claim 8, wherein the linker is formed from p-maleimidophenyl isocyanate.

10. The implantable scaffold according to claim 1, wherein the biologically active peptide is formed with a thiol-functionalized peptide.

11. The implantable scaffold according to claim 10, wherein the thiol-functionalized peptide is a cysteine containing peptide.

12. The implantable scaffold according to claim 1, wherein the biologically active peptide comprises about 5 to about 30 amino acids.

13. The implantable scaffold according to claim 1, wherein the implantable scaffold comprises a plurality of first fibers and a plurality of second fibers, the plurality of first fibers comprising the peptide conjugate polymer.

14. The implantable scaffold according to claim 13, wherein the plurality of first fibers further comprises a second polymer, the second polymer comprising a polyester polymer.

15. The implantable scaffold according to claim 13, wherein the second polymer is a poly(caprolactone).

16. The implantable scaffold according to claim 14, wherein the first polymer and the second polymer are present in a weight ratio of about 1:2 to about 5:1.

17. The implantable scaffold according to claim 13, wherein the plurality of first fibers and the plurality of second fibers form an intersecting pattern comprising a cross-hatch geometry.

18. A method of forming an implantable scaffold comprising:
   a) 3D-printing a plurality of first fibers in a first direction to form a first layer;
   b) 3D-printing a plurality of second fibers in a second direction atop the first layer to form a second layer, wherein the first and second directions are different; wherein at least one of the first fibers or the second fibers comprise the peptide-polymer conjugate according to claim 1.

19. The method according to claim 18, wherein the 3D-printing of step a) includes 3D-printing a first ink composition to form the plurality of first fibers, the first ink composition comprising a volatile solvent and the peptide-polymer conjugate; and wherein the 3D-printing of step b) includes 3D-printing a second ink composition to form the plurality of second fibers, the second ink composition comprising a volatile solvent and the peptide-polymer conjugate.

* * * * *